United States Patent [19]
Vandenbossche et al.

[11] Patent Number: 6,027,538
[45] Date of Patent: Feb. 22, 2000

[54] COMPOSITIONS FOR DYEING KERATINOUS FIBERS COMPRISING INDAZOLEAMINE DERIVATIVES AND DYEING PROCESS

[75] Inventors: Jean Jacques Vandenbossche, Begaar; Alain Lagrange, Coupvray, both of France

[73] Assignee: L'Oreal S.A., France

[21] Appl. No.: 09/138,528

[22] Filed: Aug. 24, 1998

[30] Foreign Application Priority Data

Aug. 25, 1997 [FR] France .................................. 97 10618

[51] Int. Cl.$^7$ ...................................................... A61K 7/13
[52] U.S. Cl. .......................... 8/409; 8/401; 8/407; 8/423; 8/573
[58] Field of Search ................................ 8/401, 406, 407, 8/408, 409, 410, 416, 421, 423, 573

[56] References Cited

U.S. PATENT DOCUMENTS

| | | | |
|---|---|---|---|
| 3,603,655 | 9/1971 | Berth | 8/423 |
| 3,658,455 | 4/1972 | Kalopissis et al. | 8/409 |
| 4,013,404 | 3/1977 | Parent et al. | 8/423 |
| 4,104,020 | 8/1978 | Rose | 8/416 |
| 4,168,953 | 9/1979 | Rose | 8/423 |
| 5,494,490 | 2/1996 | Audousset et al. | 8/423 |
| 5,578,087 | 11/1996 | Audousset et al. | 8/423 |
| 5,743,919 | 4/1998 | Moeller et al. | 8/423 |

FOREIGN PATENT DOCUMENTS

| | | |
|---|---|---|
| 0004368 | 10/1979 | European Pat. Off. . |
| 2 315 906 | 1/1977 | France . |
| 2 352 541 | 12/1977 | France . |
| 2 586 913 | 3/1987 | France . |
| 2 733 749 | 11/1996 | France . |
| 2 750 048 | 12/1997 | France . |
| 1 492 166 | 12/1969 | Germany . |
| 1492166 | 12/1969 | Germany . |
| 2 359 399 | 6/1975 | Germany . |
| 2527791 | 12/1976 | Germany . |
| 2 623 564 | 12/1977 | Germany . |
| 2 719 179 | 11/1978 | Germany . |
| 2719179 | 11/1978 | Germany . |
| 3 843 892 | 6/1990 | Germany . |
| 4 133 957 | 4/1993 | Germany . |
| 195 43 988 | 5/1997 | Germany . |
| 63-169571 | 7/1988 | Japan . |
| 3-10659 | 1/1991 | Japan . |
| 1 026 978 | 4/1966 | United Kingdom . |
| 1 153 196 | 5/1969 | United Kingdom . |
| WO 94/08969 | 4/1994 | WIPO . |
| WO 94/08970 | 4/1994 | WIPO . |
| WO 96/15765 | 5/1996 | WIPO . |

OTHER PUBLICATIONS

Lyell C. Behr et al., "Pyrazoles, Pyrazolines, Pyrazolidines, Indazoles, and Condensed Rings", Interscience Publishers, 1967/(no month available), pp. ix–xvi.
English Language Derwent Abstract of DE 1 492 166, Dec. 1969.
English Language Derwent Abstract of DE 2 359 399, Jun. 1975.
English Language Derwent Abstract of DE 2 623 564, Dec. 1977.
English Language Derwent Abstract of DE 2 719 179, Nov. 1978.
English Language Derwent Abstract of DE 3 843 892, Jun. 1990.
English Language Derwent Abstract of DE 4 133 957, Apr. 1993.
English Language Derwent Abstract of DE 195 43 988, May 1997.
English Language Derwent Abstract of FR 2 586 913, Mar. 1987.
English Language Derwent Abstract of FR 2 733 749, Nov. 1996.
English Language Derwent Abstract of FR 2 750 048, Dec. 1997.
English Language Derwent Abstract of JP 63–169571, Jul. 1988.
English Language Derwent Abstract of JP 3–10659, Apr. 1997.

*Primary Examiner*—Caroline D. Liott
*Attorney, Agent, or Firm*—Finnegan, Henderson, Farabow, Garrett & Dunner, L.L.P.

[57] ABSTRACT

A composition for the oxidation dyeing of keratinous fibers containing at least one coupler selected from indazoleamine derivatives and acid addition salts thereof and at least one oxidation base. Another aspect of the invention is the use of indazoleamine derivatives as coupler for the oxidation dyeing of keratinous fibers, in combination with at least one oxidation base, and the dyeing processes employing them.

25 Claims, No Drawings

COMPOSITIONS FOR DYEING KERATINOUS FIBERS COMPRISING INDAZOLEAMINE DERIVATIVES AND DYEING PROCESS

A subject-matter of the invention is a composition for the oxidation dyeing of keratinous fibers comprising at least one indazoleamine derivative as coupler and at least one oxidation base.

It is known to dye keratinous fibers, and in particular human hair, with dyeing compositions comprising oxidation dye precursors, in particular ortho- or para-phenylenediamines, ortho- or para-aminophenols, or heterocyclic compounds, generally known as oxidation bases. Oxidation dye precursors, or oxidation bases, are colourless or weakly coloured compounds which, in combination with oxidants, can give rise, by an oxidative coupling process, to coloured and colouring compounds.

It is also known that it is possible to vary the shades obtained with these oxidation bases by combining them with couplers or colouring modifiers, the latter being selected in particular from aromatic meta-diamines, meta-aminophenols, meta-diphenols and certain heterocyclic compounds, such as indole compounds.

The variety of the molecules employed as oxidation bases and couplers makes it possible to obtain a rich palette of colours.

The so-called "permanent" colouring obtained by virtue of these oxidation dyes must, furthermore, satisfy a certain number of requirements. Thus, it must be without disadvantage toxicologically, it must make it possible to obtain shades in the desired intensity and it must behave well in the face of external agents (light, weathering, washing, permanent waving, perspiration or rubbing).

The dyes must also make it possible to cover white hair and, finally, must be as non-selective as possible, that is to say must make it possible to obtain minimal differences in colouring all along the same keratinous fiber, because the fiber can exhibit different sensitivity (i.e. damage) between its tip and its root.

The use of compounds of indazole type is known in the field of hair dyeing. Patent Application DE-A-1,492,166 discloses the oxidative polycondensation of such compounds. Patent Application DE-A-2,623,564 discloses the combination of hydroxyindazoles with tetraaminopyrimidines. U.S. Pat. No. 4,013,404 discloses certain aminoindazoles and their use as oxidation dye precursors.

The inventors have now discovered that it is possible to obtain novel dyes, which are powerful, not very selective and particularly resistant and which are capable of generating intense colorations in varied shades, by using specific indazoleamine derivatives.

This discovery is at the basis of the present invention.

A subject-matter of the invention is thus a composition for the dyeing of keratinous fibers and in particular human keratinous fibers, such as the hair, characterized in that it comprises, in a medium appropriate for dyeing:

as coupler, at least one indazoleamine derivative of formula (I) and/or at least one of its addition salts with an acid:

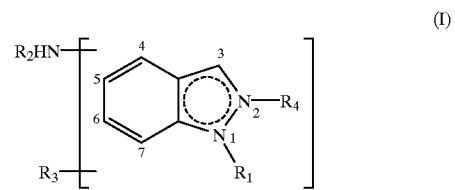

in which:
either $R_1$ denotes a hydrogen atom or a radical selected from $C_1$–$C_4$ alkyl, $C_1$–$C_4$ hydroxyalkyl, $C_1$–$C_4$ aminoalkyl, mono($C_1$–$C_4$)alkylamino($C_1$–$C_4$)alkyl, di($C_1$–$C_4$)alkylamino($C_1$–$C_4$)alkyl, ($C_1$–$C_4$)alkoxycarbonyl, ($C_1$–$C_4$)alkoxycarbonyl($C_1$–$C_4$)alkyl, $C_1$–$C_4$ acyl, ($C_1$–$C_4$)alkoxy($C_1$–$C_4$)alkyl, cyano($C_1$–$C_4$)alkyl, allyl and ($C_1$–$C_4$)alkylthiocarbonyl($C_1$–$C_4$)alkyl radicals and then $R_4$ forms a double bond with the carbon in the 3 position;

or $R_4$ denotes a radical selected from $C_1$–$C_4$ alkyl, $C_1$–$C_4$ hydroxyalkyl, $C_1$–$C_4$ aminoalkyl, mono($C_1$–$C_4$)alkylamino($C_1$–$C_4$)alkyl, di($C_1$–$C_4$) alkyl-amino ($C_1$–$C_4$)alkyl, ($C_1$–$C_4$)alkoxycarbonyl, $C_1$–$C_4$ acyl and $C_7$–$C_9$ alkylaryl radicals and a amidino radical (—C(NH$_2$)=NH) and then $R_1$ forms a double bond with the carbon adjacent to the nitrogen atom bonded to $R_1$;

$R_2$ denotes a hydrogen atom or a radical selected from $C_1$–$C_4$ alkyl, $C_1$–$C_4$ hydroxyalkyl, $C_1$–$C_4$ aminoalkyl, mono($C_1$–$C_4$)alkylamino($C_1$–$C_4$)alkyl, di($C_1$–$C_4$) alkylamino($C_1$–$C_4$)alkyl, carboxy($C_1$–$C_4$)alkyl, ($C_1$–$C_4$)alkoxy($C_1$–$C_4$)alkyl and ω-hydroxy($C_1$–$C_4$) alkoxy ($C_1$–$C_4$)alkyl radicals;

$R_3$ denotes a hydrogen atom, a bromine, chlorine or fluorine atom, or a radical selected from $C_1$–$C_4$ alkyl, $C_1$–$C_4$ hydroxyalkyl, $C_1$–$C_4$ aminoalkyl, $C_1$–$C_4$ alkoxy, ($C_1$–$C_4$) alkoxy ($C_1$–$C_4$)alkyl, mono($C_1$–$C_4$) alkylamino($C_1$–$C_4$)alkyl, di($C_1$–$C_4$)alkylamino ($C_1$–$C_4$)alkyl, $C_1$–$C_4$ perfluoroalkyl, cyano ($C_1$–$C_4$) alkyl and carboxy($C_1$–$C_4$)alkyl radicals or an amino group;

it being understood that:
when $R_1$ represents a hydrogen atom and when $R_4$ forms a double bond with the carbon in the 3 position and when $R_2$ represents a hydrogen atom or a $C_1$–$C_4$ alkyl radical, then $R_3$ cannot represent an amino group in the meta position with respect to the —NHR$_2$ group;

when $R_1$ and $R_2$ simultaneously represent a hydrogen atom and when $R_4$ forms a double bond with the carbon in the 3 position, then $R_3$ is other than a $C_1$ alkoxy radical;

and at least one oxidation base.

In the above formula (I), the $C_1$–$C_4$ alkyl and $C_1$–$C_4$ alkoxy groups can be linear or branched.

The compounds of formula (I) are known compounds, the methods of preparation of which are described in the following works:

Barton D. and Ollis W. D., "Comprehensive Organic Chemistry", Vol. 4, page 400–410, published by Pergamon Press;

Fusco R., "The Chemistry of Heterocyclic Compounds, Pyrazoles, Pyrazolines, Pyrazolidines, Indazoles and Condensed Rings", 1967, published by R. H. Wiley, N.Y.;

Katritsky A., "Comprehensive Heterocyclic Chemistry", published by Elsevier; the disclosures of which are specifically incorporated by reference herein.

The colorations obtained with the dyeing composition in accordance with the invention are varied and powerful shades which are not very selective and which exhibit excellent resistance properties both with respect to atmospheric agents, such as light and weathering, and with respect to perspiration and various treatments which hair can be subjected to (shampooings or permanent deformations).

The compounds of formula (I) in which $R_1$ denotes a hydrogen atom or a radical as defined above have a structure in accordance with the following formula (II):

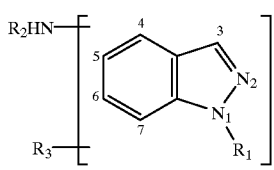

(II)

The compounds of formula (I) in which $R_4$ denotes a radical as defined above have a structure in accordance with the following formula (III):

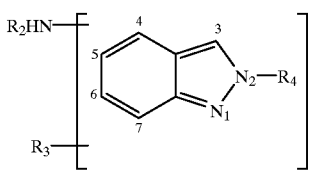

(III)

In the compounds of formulae (II) and (III), the $R_1$, $R_2$, $R_3$ and $R_4$ radicals have the same meanings as those given for the compounds of formula (I).

Mention may in particular be made, among the indazoleamine derivatives of formula (I) which can be used as couplers in the dyeing compositions in accordance with the invention, of:

4-amino-1H-indazole,
5-amino-1H-indazole,
6-amino-1H-indazole,
7-amino-1H-indazole,
4-(2'-aminoethyl)amino-1H-indazole,
5-(2'-aminoethyl)amino-1H-indazole,
4-amino-6-methyl-1H-indazole,
3-chloro-4-amino-1H-indazole,
4-amino-7-methyl-1H-indazole,
4-amino-5-methyl-1H-indazole,
4-(3'aminopropyl)amino-1H-indazole,
3-fluoro-5-amino-1H-indazole,
4-methyl-5-amino-1H-indazole,
3-methyl-5-amino-1H-indazole,
3-[2'-(N,N-diethylamino)propyl]amino-5-amino-1H-indazole,
5-(2'-aminoethyl)amino-1H-indazole,
5-amino-6-methyl-1H-indazole,
3-trifluoromethyl-5-amino-1H-indazole,
(5-amino-1H-indazol-3-yl)acetic acid,
3-chloro-5-amino 1H-indazole,
6-amino-7-chloro -1H-indazole,
5-amino-6-chloro-1H-indazole,
6-amino-7-bromo-1H-indazole,
the ethyl ester of (6-amino 3-chloro-1H-indazol-1-yl) acetic acid,
1-methoxymethyl-6-amino-1H-indazole,
1-ally-6-amino-1H-indazole,
6-amino-7-chloro-1H-indazole,
(1H-indazol-6-ylamino)acetic acid,
6-N-(2'-hydroxyethyl)amino-1H-indazole,
6-(N-propyl)amino-1H-indazole,
1-(N',N'-diethylamino)ethyl-6-amino-1H-indazole,
5-chloro-6-amino-1H-indazole,
1-(2'-cyanoethyl)-6-amino-1H-indazole,
3-(6-amino-1H-indazol-1-yl)thiopropionamide,
6-(N-ethyl)amino-1H-indazole,
3-methyl-6-amino-1H-indazole,
5-methyl-6-amino-1H-indazole,
3-bromo-6-amino-1H-indazole,
3-chloro-6-amino-1H-indazole,
6-amino-7-methyl-1H-indazole,
4-chloro-6-amino-1H-indazole,
5-methyl-7-(2'-methoxyethyl)amino-1H-indazole,
5-methyl-7-(2'-hydroxyethyl)amino-1H-indazole,
6-methyl-7-[2'-(2"-hydroxyethoxy)ethyl]amino-1H-indazole,
4-(2'-N,N-dipropyl)ethyl-7-amino-1H-indazole,
4-(2'-aminoethyl)-7-amino-1H-indazole,
4-cyanomethyl-7-amino-1H-indazole,
2-(2'-N,N-dimethyl)ethyl-7-amino-1H-indazole,
3-methyl-7-amino-1H-indazole,
4-chloro-7-amino-1H-indazole,
7-[N-(2'-aminoethyl)]amino-1H-indazole,
4-chloro-5-methyl-7-amino-1H-indazole,
5-chloro-7-amino-1H-indazole,
5-methyl-7-amino-1H-indazole,
6-methyl-7-amino-1H-indazole,
1-methyl-4-amino-1H-indazole,
1-methyl-5-amino-1H-indazole,
1-methyl-6-amino-1H-indazole,
1,3-dimethyl-6-amino-1H-indazole,
1-methyl-7-amino-1H-indazole,
1,5-dimethyl-7-amino-1H-indazole,
1-methyl-3-bromo-7-(N-methyl)amino-1H-indazole,
1-methyl-3-chloro-7-(N-methyl)amino-1H-indazole,
1-methyl-5-chloro-7-amino-1H-indazole,
1-methyl-7-(N-methyl)amino-1H-indazole,
1-methyl-6-chloro-7-amino-1H-indazole,
1-ethyl-7-amino-1H-indazole,
2-methyl-3-amino-5-trifluoromethyl-2H-indazole,
2-methyl-3-(N-methyl)amino-2H-indazole,
2-methyl-4-amino-2H-indazole,
2,6-dimethyl-4-amino-2H-indazole,
2-methyl-5-amino-2H-indazole,
2,3-dimethyl-5-amino-2H-indazole,
2-methyl-6-amino-2H-indazole,
2-methyl-7-amino-2H-indazole,
2-ethyl-5-amino-2H-indazole,
2-ethyl-6-amino-2H-indazole, 2-benzyl-4-amino-2H-indazole,
2-[2'-(N, N-dimethylamino)ethyl]-6-amino-2H-indazole,
2-[2'-(N, N-diethylamino)ethyl]-6-amino-2H-indazole,
2-amidino-5-amino-2H-indazole,
2-amidino-6-amino-2H-indazole,
2-amidino-7-amino-2H-indazole,
and their addition salts with an acid.

The indazoleamine derivative or derivatives of formula (I) and/or the addition salt or their addition salts with an acid preferably represent from approximately 0.0005 to approximately 12% by weight of the total weight of the dyeing composition and more preferably still from approximately 0.005 to approximately 6% by weight of this weight.

The nature of the oxidation base or bases which can be used in the dyeing composition according to the invention is not critical. This or these oxidation base or bases are preferably selected from para-phenylenediamines, bisphenylalkylenediamines, para-aminophenols, ortho-aminophenols, heterocyclic bases and their addition salts with an acid.

Mention may in particular be made, among the para-phenylenediamines which can be used as oxidation bases in the dyeing composition in accordance with the invention, of the compounds corresponding to the following formula (IV) and their addition salts with an acid:

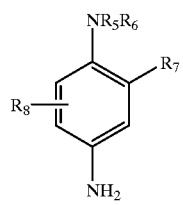

(IV)

in which:
$R_5$ represents a hydrogen atom or a $C_1$–$C_4$ alkyl, $C_1$–$C_4$ monohydroxyalkyl, $C_2$–$C_4$ polyhydroxyalkyl or ($C_1$–$C_4$)alkoxy($C_1$–$C_4$)alkyl radical;
$R_6$ represents a hydrogen atom or a $C_1$–$C_4$ alkyl, $C_1$–$C_4$ monohydroxyalkyl or $C_2$–$C_4$ polyhydroxyalkyl radical;
$R_7$ represents a hydrogen atom, a halogen atom, such as a chlorine atom, or a $C_1$–$C_4$ alkyl, sulpho, carboxyl, $C_1$–$C_4$ monohydroxyalkyl or $C_1$–$C_4$ hydroxyalkoxy radical;
$R_8$ represents a hydrogen atom or a $C_1$–$C_4$ alkyl radical.

In the above formula (IV) and when $R_7$ is other than a hydrogen atom, then $R_5$ and $R_6$ preferably represent a hydrogen atom and $R_7$ is preferably identical to $R_8$, and, when $R_7$ represents a halogen atom, then $R_5$, $R_6$ and $R_8$ preferably represent a hydrogen atom.

Mention may more particularly be made, among the para-phenylenediamines of formula (IV) above, of para-phenylenediamine, para-toluylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 4-amino-1-[(β-methoxyethyl)amino] benzene, 2-chloro-para-phenylenediamine and their addition salts with an acid.

Mention may in particular be made, among bisphenylalkylenediamines which can be used as oxidation bases in the dyeing composition in accordance with the invention, of the compounds corresponding to the following formula (V) and their addition salts with an acid:

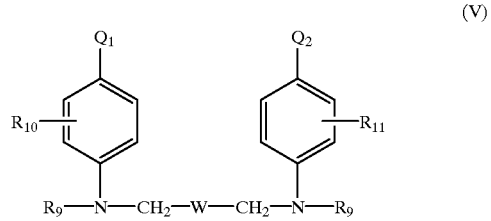

(V)

in which:
$Q_1$ and $Q_2$ independently represent a hydroxyl or $NHR_{12}$ radical in which $R_{12}$ represents a hydrogen atom or a $C_1$–$C_4$ alkyl radical,
$R_9$ represents a hydrogen atom or a $C_1$–$C_4$ alkyl, $C_1$–$C_4$ monohydroxyalkyl, $C_2$–$C_4$ polyhydroxyalkyl or $C_1$–$C_4$ aminoalkyl radical, the amino residue of which can be substituted,
$R_{10}$ and $R_{11}$ independently represent a hydrogen or halogen atom or a $C_1$–$C_4$ alkyl radical,
W represents a radical selected from:

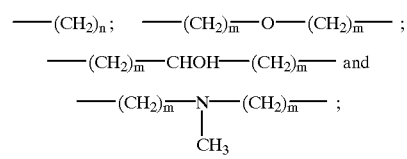

in which n is an integer ranging from 0 to 8 and m is an integer ranging from 0 to 4.

Mention may more particularly be made, among the bisphenylalkylenediamines of formula (V) above, of N,N'-bis(β-hydroxyethyl)-N,N'-bis(4'-aminophenyl)-1,3-diamino-2-propanol, N,N'-bis(β-hydroxyethyl)-N,N'-bis(4'-aminophenyl)ethylenediamine, N,N'-bis(4-aminophenyl) tetramethylenediamine, N,N'-bis(β-hydroxyethyl)-N,N'-bis (4-aminophenyl)tetramethylenediamine, N,N'-bis(4-methylaminophenyl)tetramethylenediamine, N,N'-bis-(ethyl)-N,N'-bis(4'-amino-3'-methylphenyl)ethylenediamine and their addition salts with an acid.

Among the bisphenylalkylenediamines of formula (V) above, N,N'-bis(β-hydroxyethyl)-N,N'-bis(4'-aminophenyl)-1,3-diamino-2-propanol and one of its addition salts with an acid are particularly preferred.

Mention may in particular be made, among para-aminophenols which can be used as oxidation bases in the dyeing composition in accordance with the invention, of the compounds corresponding to the following formula (VI) and their addition salts with an acid.

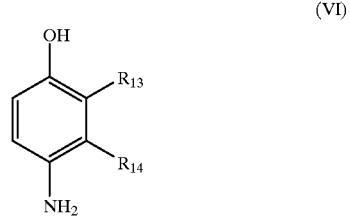

(VI)

in which:
$R_{13}$ represents a hydrogen atom or a $C_1$–$C_4$ alkyl, $C_1$–$C_4$ monohydroxyalkyl, ($C_1$–$C_4$)alkoxy($C_1$–$C_4$)alkyl or $C_1$–$C_4$ aminoalkyl radical;

$R_{14}$ represents a hydrogen or fluorine atom or a $C_1$–$C_4$ alkyl, $C_1$–$C_4$ monohydroxyalkyl, $C_2$–$C_4$ polyhydroxyalkyl, $C_1$–$C_4$ aminoalkyl, cyano($C_1$–$C_4$) alkyl or ($C_1$–$C_4$)alkoxy($C_1$–$C_4$)alkyl radical;

it being understood that at least one of the $R_{13}$ or $R_{14}$ radicals represents a hydrogen atom.

Mention may more particularly be made, among the para-aminophenols of formula (VI) above, of para-aminophenol, 4-amino-3-methylphenol, 4-amino-3-fluorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(aminomethyl)phenol, 4-amino-2-[(β-hydroxyethyl)aminomethyl]phenol and their addition salts with an acid.

Mention may in particular be made, among ortho-aminophenols which can be used as oxidation bases in the dyeing composition according to the invention, of 2-aminophenol, 2-amino-1-hydroxy-5-methylbenzene, 2-amino-1-hydroxy-6-methylbenzene, 5-acetamido-2-aminophenol and their addition salts with an acid.

Mention may in particular be made, among heterocyclic bases which can be used as oxidation bases in the dyeing composition according to the invention, of pyridine derivatives, pyrimidine derivatives, pyrazole derivatives and their addition salts with an acid.

Mention may more particularly be made, among pyridine derivatives, of the compounds disclosed, for example, in Patents GB 1,026,978 and GB 1,153,196, the disclosures of which are specifically incorporated by reference herein, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine and their addition salts with an acid.

Mention may more particularly be made, among pyrimidine derivatives, of the compounds disclosed, for example, in German Patent DE 2,359,399 or Japanese Patents JP 88-169,571 and JP 91-10659 or Patent Application WO 96/15765, the disclosures of which are specifically incorporated by reference herein, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine or 2,5,6-triaminopyrimidine, and pyrazolopyrimidine derivatives, such as those mentioned in Patent Application FR-A-2,750,048, the disclosure of which is specifically incorporated by reference herein, among which mention may be made of pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidin-3,7-diamine, 2,6-dimethylpyrazolo[1,5-a]pyrimidin-3,7-diamine or 2,5N7,N7-tetramethylpyrazolo[1,5a]pyrimidin-3,7-diamine, their addition salts and their tautomeric forms, when a tautomeric equilibrium exists.

Mention may more particularly be made, among pyrazole derivatives, of the compounds disclosed in Patents DE 3,843,892 and DE 4,133,957 and Patent Applications WO 94/08969, WO 94/08970, FR-A-2,733,749 and DE 195 43 988, the disclosures of which are specifically incorporated by reference herein, such as 4,5-diamino-1-methylpyrazole, 3,4-diaminopyrazole, 4,5-diamino-1-(4'-chlorobenzyl) pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-(hydroxymethyl)pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-(methylamino)pyrazole, 3,5-diamino-4-(β-hydroxyethyl)amino-1-methylpyrazole and their addition salts with an acid.

According to the invention, the oxidation base or bases preferably represent from approximately 0.0005 to approximately 12% by weight of the total weight of the dyeing composition and more preferably still from approximately 0.005 to approximately 6% by weight of this weight.

The dyeing composition in accordance with the invention can also contain one or more additional couplers other than the indazoleamine derivatives of formula (I) and/or one or more direct dyes, so as to vary or enrich with highlights the shades obtained.

The additional couplers which can be used in the composition in accordance with the invention can be selected from couplers conventionally used in oxidation dyeing, among which may in particular be mentioned meta-phenylenediamines, metaaminophenols, meta-diphenols and heterocyclic couplers, such as, for example, indole derivatives or indoline derivatives, and their addition salts with an acid.

These couplers can in particular be selected from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-N-(β-hydroxyethyl)amino-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline and their addition salts with an acid.

When they are present, these additional couplers preferably represent from approximately 0.0005 to approximately 5% by weight of the total weight of the dyeing composition and more preferably still from approximately 0.005 to approximately 3% by weight of this weight.

The addition salts with an acid of the indazoleamine derivative or derivatives of formula (I) and/or of the oxidation base or bases and/or of the additional couplers which can be used in the dyeing composition of the invention are selected in particular from hydrochlorides, hydrobromides, sulphates and tartrates, lactates and acetates.

The medium appropriate for the dyeing (or vehicle) is generally composed of water or of a mixture of water and at least one organic solvent for dissolving the compounds which would not be sufficiently soluble in water. Mention may be made, as organic solvent, of, for example, lower $C_1$–$C_4$ alkanols, such as ethanol and isopropanol, glycerol, glycols and glycol ethers, such as 2-butoxyethanol, propylene glycol, propylene glycol monomethyl ether, or diethylene glycol monoethyl ether and monomethyl ether, and aromatic alcohols, such as benzyl alcohol or phenoxyethanol, the analogous products and their mixtures.

The solvents can be present in proportions preferably ranging from approximately 1 to approximately 40% by weight with respect to the total weight of the dyeing composition and more preferably still from approximately 5 to approximately 30% by weight.

The pH of the dyeing composition in accordance with the invention generally ranges from 3 to 12. It can be adjusted to the desired value by means of acidifying or basifying agents commonly used in dyeing keratinous fibers.

Mention may be made, among acidifying agents, by way of example, of inorganic or organic acids, such as hydrochloric acid, orthophosphoric acid, carboxylic acids, such as tartaric acid, citric acid or lactic acid, or sulphonic acids.

Mention may be made, among basifying agents, by way of example, of ammonia, alkaline carbonates, alkanolamines, such as mono-, di- and triethanolamines and their derivatives, sodium hydroxide, potassium hydroxide and the compounds of following formula (VII):

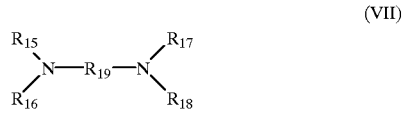

(VII)

in which $R_{19}$ is a propylene residue optionally substituted by a hydroxyl group or a $C_1$–$C_4$ alkyl radical and $R_{15}$, $R_{16}$, $R_{17}$ and $R_{18}$ independently represent a hydrogen atom or a $C_1$–$C_4$ alkyl or $C_1$–$C_4$ hydroxyalkyl radical.

The dyeing composition in accordance with the invention can also contain various adjuvants conventionally used in hair dyeing compositions, such as anionic, cationic, non-ionic, amphoteric or zwitterionic surface-active agents or their mixtures, anionic, cationic, non-ionic, amphoteric or zwitterionic polymers or their mixtures, inorganic or organic thickening agents, antioxidizing agents, penetrating agents, sequestering agents, fragrances, buffers, dispersing agents, conditioning agents, such as, for example, silicones, film-forming agents, preservatives or opacifying agents.

Of course, a person skilled in the art will take care to choose the optional additional compound or compounds mentioned above so that the advantageous properties intrinsically attached to the dyeing composition according to the invention are not, or not substantially, detrimentally affected by the envisaged addition or additions.

The dyeing composition in accordance with the invention can be provided in various forms, such as in the form of liquids, creams or gels, or in any other form appropriate for carrying out dyeing of keratinous fibers and in particular of human hair.

Another aspect of the invention is the use of the indazoleamine derivatives of formula (I) above as coupler, in combination with at least one oxidation base, for the oxidation dyeing of keratinous fibers and in particular of human keratinous fibers, such as hair.

Another aspect of the invention is a process for the oxidation dyeing of keratinous fibers and in particular of human keratinous fibers, such as hair, employing the dyeing composition as defined above.

According to this process, at least one dyeing composition as defined above is applied to the fibers, the colour being developed at acidic, neutral or alkaline pH using an oxidizing agent which is added only at the time of use to the dyeing composition or which is present in an oxidizing composition applied simultaneously or sequentially in a separate fashion.

According to a particularly preferred embodiment of the dyeing process according to the invention, the dyeing composition as defined above is mixed, at the time of use, with an oxidizing composition containing, in a medium appropriate for dyeing, at least one oxidizing agent present in an amount sufficient to develop a coloration. The mixture obtained is subsequently applied to the keratinous fibers and left in contact for approximately 3 to approximately 50 minutes, preferably approximately 5 to approximately 30 minutes, after which the hair is rinsed, washed with a shampoo, rinsed again and dried.

The oxidizing agent present in the oxidizing composition as defined above can be selected from oxidizing agents conventionally used for the oxidation dyeing of keratinous fibers, among which may be mentioned hydrogen peroxide, urea hydrogen peroxide, alkali metal bromates, persalts, such as perborates and persulphates, peracids and enzymes. Hydrogen peroxide is particularly preferred.

The pH of the oxidizing composition containing the oxidizing agent as defined above is such that, after mixing with the dyeing composition, the pH of the resulting composition applied to the keratinous fibers preferably ranges from approximately 3 to approximately 12 and more preferably still from 5 to 11. It is adjusted to the desired value by means of acidifying or basifying agents commonly used in dyeing keratinous fibers and as defined above.

The oxidizing composition as defined above can also contain various adjuvants conventionally used in hair dyeing compositions as defined above.

The composition which is finally applied to the keratinous fibers can be provided in various forms, such as in the form of liquids, creams or gels, or in any other form appropriate for carrying out dyeing of keratinous fibers in particular of human hair.

Another aspect of the invention is a multi-compartment dyeing device or a multi-compartment dyeing "kit" or any other multi-compartment packaging system, a first compartment of which contains the dyeing composition as defined above and a second compartment of which contains the oxidizing composition as defined above. These devices can be equipped with a means which makes it possible to deliver the desired mixture onto the hair, such as the devices described in Patent FR-2,586,913, the disclosure of which is specifically incorporated by reference herein.

A preferred subgenus of the present invention involves a composition for dyeing keratinous fibers comprising in a medium appropriate for dyeing, at least one coupler selected from compounds of formula I and acid addition salts thereof and at least one heterocyclic oxidation base, preferably pyrazolopyrimidine compounds or pyrazole compounds, more preferably, pyrazolo[1,5-a]pyrimidine-3,7-diamine salts, such as pyrazolo[1,5-a]pyrimidine-3,7-diamine.2HCl or 4,5-diamino-1,3-dimethylpyrazole salts, such as 4,5-diamino-1,3-dimethylpyrazole.2HCl, more preferably at neutral pH. Most preferably 1-methyl-4-amino-1H-indazole-2HCl and pyrazolo[1,5-a]pyrimidine-3,7-diamine.2HCl are utilized at neutral pH to obtain a powerful purple color.

The following examples are intended to illustrate the invention without limiting the scope thereof.

EXAMPLES 1 TO 20

The following dyeing compositions were prepared:

| | |
|---|---|
| Coupler | 0.003 mol |
| Base | 0.003 mol |
| Absolute alcohol | 30 g |
| 35% Aqueous sodium metabisulphite solution | 1.3 g |
| 20% Aqueous ammonia solution | q.s. pH 10 |
| Water | q.s. for 100 g |

These dyeing compositions were prepared for the following couplers in accordance with the invention:

C1: 2-methyl-4-amino-2H-indazole.2HCl
C2: 2-methyl-5-amino-2H-indazole.2HCl
C3: 2-methyl-6-amino-2H-indazole.2HCl
C4: 2-methyl-7-amino-2H-indazole.HCl
C5: 1-methyl-4-amino-1H-indazole.2HCl
C6: 1-methyl-5-amino-1H-indazole-HCl.H$_2$O
C7: 1-methyl-6-amino-1H-indazole
C8: 1-methyl-7-amino-1H-indazole.HCl.H$_2$O
C9: 4-amino-1H-indazole.2HCl
C10: 7-amino-1H-indazole.2HCl For each coupler, two dyeing compositions were prepared, each with a different oxidation base: para-phenylenediamine (PPD) or para-aminophenol (PAP).

At the time of use, each dyeing composition was mixed with an equal weight of 20-volume hydrogen peroxide (6% by weight).

Each mixture obtained was applied for 30 minutes to locks of natural grey hair containing 90% of white hairs, at the rate of 28 g per 3 g of hair. After rinsing, washing with a standard shampoo and drying, the locks were dyed in the shades which appear in Table I below:

TABLE I

| Example | Coupler | Base | Shade obtained |
|---|---|---|---|
| 1 | C1 | PPD | Deep purple |
| 2 | C1 | PAP | Pinkish coppery |
| 3 | C2 | PPD | Aubergine with golden highlights |
| 4 | C2 | PAP | Copper blond |
| 5 | C3 | PPD | Dark grey with aubergine highlights |
| 6 | C3 | PAP | Honey |
| 7 | C4 | PPD | Bright blue-purple |
| 8 | C4 | PAP | Very intense rosewood |
| 9 | C5 | PPD | Deep-purple chestnut |
| 10 | C5 | PAP | Golden rosewood |
| 11 | C6 | PPD | Chestnut |
| 12 | C6 | PAP | Coppery dark blond |
| 13 | C7 | PPD | Ash grey with deep-purple highlights |
| 14 | C7 | PAP | Slightly coppery blond |
| 15 | C8 | PPD | Purplish grey-blue |
| 16 | C8 | PAP | Slightly coppery golden blond |
| 17 | C9 | PPD | Chestnut-deep purple |
| 18 | C9 | PAP | Rosewood |
| 19 | C10 | PPD | Intense blue-purple |
| 20 | C10 | PAP | Hazel |

We claim:

1. A composition for dyeing keratinous fiber comprising, in a medium appropriate for dyeing:

at least one coupler selected from indazoleamine derivatives of formula (I) and acid addition salts thereof:

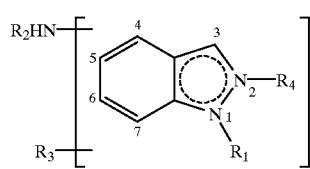

in which:

R$_1$ denotes a radical selected from C$_1$–C$_4$ alkyl, C$_1$–C$_4$ hydroxyalkyl, C$_1$–C$_4$ aminoalkyl, mono(C$_1$–C$_4$)alkylamino(C$_1$–C$_4$)alkyl, di(C$_1$–C$_4$)alkylamino(C$_1$–C$_4$)alkyl, (C$_1$–C$_4$)alkoxycarbonyl, (C$_1$–C$_4$)alkoxycarbonyl(C$_1$–C$_4$)alkyl, C$_1$–C$_4$ acyl, (C$_1$–C$_4$)alkoxy(C$_1$–C$_4$)alkyl, cyano(C$_1$–C$_4$)alkyl, allyl and (C$_1$–C$_4$)alkylthiocarbonyl(C$_1$–C$_4$)alkyl radicals and then R$_4$ forms a double bond with the carbon in the 3 position;

R$_2$ denotes a hydrogen atom or a radical selected from C$_1$–C$_4$ alkyl, C$_1$–C$_4$ hydroxyalkyl, C$_1$–C$_4$ aminoalkyl, mono(C$_1$–C$_4$)alkylamino(C$_1$–C$_4$)alkyl, di(C$_1$–C$_4$)alkylamino(C$_1$–C$_4$)alkyl, carboxy(C$_1$–C$_4$)alkyl, (C$_1$–C$_4$)alkoxy(C$_1$–C$_4$)alkyl and ω-hydroxy(C$_1$–C$_4$)alkoxy(C$_1$–C$_4$)alkyl radicals; and R$_3$ denotes a hydrogen atom, a bromine, chlorine or fluorine atom, or a radical selected from C$_1$–C$_4$ alkyl, C$_1$–C$_4$ hydroxyalkyl, C$_1$–C$_4$ aminoalkyl, C$_1$–C$_4$ alkoxy, C$_1$–C$_4$ alkoxy (C$_1$–C$_4$)alkyl, mono(C$_1$–C$_4$)alkylamino(C$_1$–C$_4$)alkyl di(C$_1$–C$_4$)alkylamino(C$_1$–C$_4$)alkyl, C$_1$–C$_4$ perfluoroalkyl, cyano(C$_1$–C$_4$)alkyl and carboxy(C$_1$–C$_4$)alkyl radicals; or R$_4$ denotes a radical selected from C$_1$–C$_4$ alkyl, C$_1$–C$_4$ hydroxyalkyl, C$_1$–C$_4$ aminoalkyl, mono(C$_1$–C$_4$)alkylamino(C$_1$–C$_4$)alkyl, di(C$_1$–C$_4$)alkylamino(C$_1$–C$_4$)alkyl, (C$_1$–C$_4$)alkoxycarbonyl, C$_1$–C$_4$ acyl and C$_7$–C$_9$ alkylaryl radicals and an amidino radical (—C(NH$_2$)=NH) and then R$_1$ forms a double bond with the carbon adjacent to the nitrogen atom bonded to R$_1$;

R$_2$ denotes a hydrogen atom or a radical selected from C$_1$–C$_4$ alkyl, C$_1$–C$_4$ hydroxyalkyl, C$_1$–C$_4$ aminoalkyl, mono(C$_1$–C$_4$)alkylamino(C$_1$–C$_4$)alkyl, di(C$_1$–C$_4$)alkylamino(C$_1$–C$_4$)alkyl, carboxy(C$_1$–C$_4$)alkyl, (C$_1$–C$_4$)alkoxy(C$_1$–C$_4$)alkyl and ω-hydroxy(C$_1$–C$_4$)alkoxy(C$_1$–C$_4$)alkyl radicals; and R$_3$ denotes a hydrogen atom, a bromine, chlorine or fluorine atom, or a radical selected from C$_1$–C$_4$ alkyl, C$_1$–C$_4$ hydroxyalkyl, C$_1$–C$_4$ aminoalkyl, C$_1$–C$_4$ alkoxy, C$_1$–C$_4$ alkoxy (C$_1$–C$_4$)alkyl, mono(C$_1$–C$_4$)alkylamino(C$_1$–C$_4$)alkyl, di(C$_1$–C$_4$)alkylamino(C$_1$–C$_4$)alkyl, C$_1$–C$_4$ perfluoroalkyl, cyano(C$_1$–C$_4$)alkyl and carboxy(C$_1$–C$_4$)alkyl radicals or an amino group;

and at least one oxidation base.

2. A composition according to claim 1, wherein said compounds of formula (I) have a structure in accordance with formula (II):

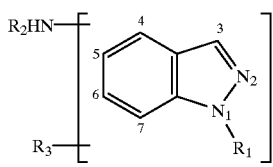

(II)

in which:
R$_1$ denotes a radical selected from C$_1$–C$_4$ alkyl, C$_1$–C$_4$ hydroxyalkyl, C$_1$–C$_4$ aminoalkyl, mono(C$_1$–C$_4$)alkylamino(C$_1$–C$_4$)alkyl, di(C$_1$–C$_4$)alkylamino(C$_1$–C$_4$)alkyl, (C$_1$–C$_4$)alkoxycarbonyl, (C$_1$–C$_4$)alkoxycarbonyl(C$_1$–C$_4$)alkyl, C$_1$–C$_4$ acyl, (C$_1$–C$_4$)alkoxy(C$_1$–C$_4$)alkyl, cyano(C$_1$–C$_4$)alkyl, allyl and (C$_1$–C$_4$)alkylthiocarbonyl(C$_1$–C$_4$)alkyl radicals;

R$_2$ denotes a hydrogen atom or a radical selected from C$_1$–C$_4$ alkyl, C$_1$–C$_4$ hydroxyalkyl, C$_1$–C$_4$ aminoalkyl, mono(C$_1$–C$_4$)alkylamino(C$_1$–C$_4$)alkyl, di(C$_1$–C$_4$)alkylamino(C$_1$–C$_4$)alkyl, carboxy(C$_1$–C$_4$)alkyl, (C$_1$–C$_4$)alkoxy(C$_1$–C$_4$)alkyl and ω-hydroxy(C$_1$–C$_4$)alkyl radicals;

R$_3$ denotes a hydrogen atom, a bromine, chlorine or fluorine atom, or a radical selected from C$_1$–C$_4$ alkyl, C$_1$–C$_4$ hydroxyalkyl, C$_1$–C$_4$ aminoalkyl, C$_1$–C$_4$ alkoxy, C$_1$–C$_4$ alkoxy (C$_1$–C$_4$)alkyl, mono(C$_1$–C$_4$)alkylamino(C$_1$–C$_4$)alkyl, di(C$_1$–C$_4$)alkylamino(C$_1$–C$_4$)alkyl, C$_1$–C$_4$ perfluoroalkyl, cyano(C$_1$–C$_4$)alkyl and carboxy(C$_1$–C$_4$)alkyl radicals.

3. A composition according to claim 1, wherein when R$_4$ denotes a radical, said compounds of formula (I) have a structure in accordance with formula (III):

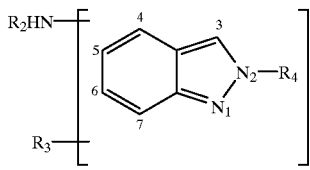

(III)

in which:
R$_4$ denotes a radical selected from C$_1$–C$_4$ alkyl, C$_1$–C$_4$ hydroxyalkyl, C$_1$–C$_4$ aminoalkyl, mono(C$_1$–C$_4$)alkylamino(C$_1$–C$_4$)alkyl, di(C$_1$–C$_4$)alkylamino(C$_1$–C$_4$)alkyl, (C$_1$–C$_4$)alkoxycarbonyl, C$_1$–C$_4$ acyl and C$_7$–C$_9$ alkylaryl radicals and an amidino radical (—C(NH$_2$)=NH);

R$_2$ denotes a hydrogen atom or a radical selected from C$_1$–C$_4$ alkyl, C$_1$–C$_4$ hydroxyalkyl, C$_1$–C$_4$ aminoalkyl, mono(C$_1$–C$_4$)alkylamino(C$_1$–C$_4$)alkyl, di(C$_1$–C$_4$)alkylamino(C$_1$–C$_4$)alkyl, carboxy(C$_1$–C$_4$)alkyl, (C$_1$–C$_4$)alkoxy(C$_1$–C$_4$)alkyl and ω-hydroxy(C$_1$–C$_4$)alkoxy(C$_1$–C$_4$)alkyl radicals; and R$_3$ denotes a hydrogen atom, a bromine, chlorine or fluorine atom, or a radical selected from C$_1$–C$_4$ alkyl, C$_1$–C$_4$ hydroxyalkyl, C$_1$–C$_4$ aminoalkyl, C$_1$–C$_4$ alkoxy, C$_1$–C$_4$ alkoxy (C$_1$–C$_4$)alkyl, mono(C$_1$–C$_4$)alkylamino(C$_1$–C$_4$)alkyl, di(C$_1$–C$_4$)alkylamino(C$_1$–C$_4$)alkyl, C$_1$–C$_4$ perfluoroalkyl, cyano(C$_1$–C$_4$)alkyl and carboxy(C$_1$–C$_4$)alkyl radicals or an amino group.

4. A composition according to claim 1, wherein said indazoleamine derivatives of formula (I) are selected from:

the ethyl ester of (6-amino-3-chloro-1H-indazol-1-yl)acetic acid,
1-methoxymethyl-6-amino-1H-indazole,
1-allyl-6-amino-1H-indazole,
1-(N', N'-diethylamino)ethyl-6-amino-1H-indazole,
1-(2'-cyanoethyl)-6-amino-1H-indazole,
3-(6-amino-1H-indazol-1-yl)thiopropionamide,
1-methyl-4-amino-1H-indazole,
1-methyl-5-amino-1H-indazole,
1-methyl-6-amino-1H-indazole,
1,3-dimethyl-6-amino-1H-indazole,
1-methyl-7-amino-1H-indazole,
1,5-dimethyl-7-amino-1H-indazole,
1-methyl-3-bromo-7-(N-methyl)amino-1H-indazole,
1-methyl-3-chloro-7-(N-methyl)amino-1H-indazole,
1-methyl-5-chloro-7-amino-1H-indazole,
1-methyl-7-(N-methyl)amino-1H-indazole,
1-methyl-6-chloro-7-amino-1H-indazole,
1-ethyl-7-amino-1H-indazole,
2-methyl-3-amino-5-trifluoromethyl-2H-indazole,
2-methyl-3-(N-methyl)amino-2H-indazole,
2-methyl-4-amino-2H-indazole,
2,6-dimethyl-4-amino-2H-indazole,
2-methyl-5-amino-2H-indazole,
2,3-dimethyl-5-amino-2H-indazole,
2-methyl-6-amino-2H-indazole,
2-methyl-7-amino-2H-indazole,
2-ethyl-5-amino-2H-indazole,
2-ethyl-6-amino-2H-indazole,
2-benzyl-4-amino-2H-indazole,
2-[2'-(N,N-dimethylamino)ethyl]-6-amino-2H-indazole,
2-[2'-(N,N-diethylamino)ethyl]-6-amino-2H-indazole,
2-amidino-5-amino-2-indazole,
2-amidino-6-amino-2H-indazole, and
2-amidino-7-amino-2H-indazole,
and their acid addition salts.

5. A composition according to claim 1, wherein said keratinous fiber is human keratinous fiber.

6. A composition according to claim 5, wherein said human keratinous fiber is human hair.

7. A composition according to claim 1, wherein said at least one coupler is present in an amount ranging from 0.0005 to 12% by weight relative to the total weight of said composition.

8. A composition according to claim 7, wherein said at least one coupler is present in an amount ranging from 0.005 to 6% by weight relative to the total weight of said composition.

9. A composition according to claim 1, wherein said at least one oxidation base is selected from para-phenylenediamines, bisphenylalkylenediamines, para-aminophenols, ortho-aminophenols, heterocyclic bases and their acid addition salts.

10. A composition according to claim 1, wherein said acid addition salts are selected from hydrochlorides, hydrobromides, sulphates, tartrates, lactates and acetates.

11. A composition according to claim 1, wherein said at least one oxidation base is present in an amount ranging from 0.0005 to 12% by weight relative to the total weight of said composition.

12. A composition according to claim 11, wherein said at least one oxidation base is present in an amount ranging from 0.005 to 6% by weight relative to the total weight of said composition.

13. A composition according to claim 1, wherein said composition further comprises at least one additional coupler other than said indazoleamine derivatives of formula (I) and acid addition salts thereof and/or at least one direct dye.

14. A method of dyeing keratinous fiber comprising the steps of:

including at least one coupler and at least one oxidation base in a composition; and thereafter oxidation dyeing keratinous fiber with said composition, wherein said coupler is selected from indazoleamine derivatives of formula (I) and acid addition salts thereof:

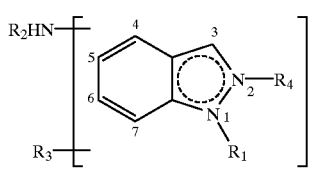

(I)

in which:

$R_1$ denotes a radical selected from $C_1$–$C_4$ alkyl, $C_1$–$C_4$ hydroxyalkyl, $C_1$–$C_4$ aminoalkyl, mono($C_1$–$C_4$) alkylamino($C_1$–$C_4$)alkyl, di($C_1$–$C_4$)alkylamino ($C_1$–$C_4$)alkyl, ($C_1$–$C_4$)alkoxycarbonyl, ($C_1$–$C_4$) alkoxycarbonyl($C_1$–$C_4$)alkyl, $C_1$–$C_4$ acyl, ($C_1$–$C_4$) alkoxy($C_1$–$C_4$)alkyl, cyano($C_1$–$C_4$)alkyl, allyl and ($C_1$–$C_4$)alkylthiocarbonyl($C_1$–$C_4$)alkyl radicals and then $R_4$ forms a double bond with the carbon in the 3 position;

$R_2$ denotes a hydrogen atom or a radical selected from $C_1$–$C_4$ alkyl, $C_1$–$C_4$ hydroxyalkyl, $C_1$–$C_4$ aminoalkyl, mono($C_1$–$C_4$)alkylamino($C_1$–$C_4$)alkyl, di($C_1$–$C_4$) alkylamino($C_1$–$C_4$)alkyl, carboxy($C_1$–$C_4$)alkyl, ($C_1$–$C_4$)alkoxy($C_1$–$C_4$)alkyl and ω-hydroxy($C_1$–$C_4$) alkoxy($C_1$–$C_4$)alkyl radicals; and $R_3$ denotes a hydrogen atom, a bromine, chlorine or fluorine atom, or a radical selected from $C_1$–$C_4$ alkyl, $C_1$–$C_4$ hydroxyalkyl, $C_1$–$C_4$ aminoalkyl, $C_1$–$C_4$ alkoxy, $C_1$–$C_4$ alkoxy ($C_1$–$C_4$)alkyl, mono($C_1$–$C_4$) alkylamino($C_1$–$C_4$)alkyl, di($C_1$–$C_4$)alkylamino ($C_1$–$C_4$)alkyl, $C_1$–$C_4$ perfluoroalkyl, cyano($C_1$–$C_4$) alkyl and carboxy($C_1$–$C_4$)alkyl radicals; or $R_4$ denotes a radical selected from $C_1$–$C_4$ alkyl, $C_1$–$C_4$ hydroxyalkyl, $C_1$–$C_4$ aminoalkyl, mono($C_1$–$C_4$) alkylamino($C_1$C$_4$)alkyl, di($C_1$–$C_4$)alkylamino($C_1$–$C_4$) alkyl, ($C_1$–$C_4$)alkoxycarbonyl, $C_1$–$C_4$ acyl and $C_7$–$C_9$ alkylaryl radicals and an amidino radical (—C(NH$_2$) =NH) and then $R_1$ forms a double bond with the carbon adjacent to the nitrogen atom bonded to $R_1$;

$R_2$ denotes a hydrogen atom or a radical selected from $C_1$–$C_4$ alkyl, $C_1$–$C_4$ hydroxyalkyl, $C_1$–$C_4$ aminoalkyl, mono($C_1$–$C_4$)alkylamino($C_1$–$C_4$)alkyl, di($C_1$–$C_4$) alkylamino($C_1$–$C_4$)alkyl, carboxy($C_1$–$C_4$)alkyl, ($C_1$–$C_4$)alkoxy($C_1$–$C_4$)alkyl and ω-hydroxy($C_1$–$C_4$) alkoxy($C_1$–$C_4$)alkyl radicals; and $R_3$ denotes a hydrogen atom, a bromine, chlorine or fluorine atom, or a radical selected from $C_1$–$C_4$ alkyl, $C_1$–$C_4$ hydroxyalkyl, $C_1$–$C_4$ aminoalkyl, $C_1$–$C_4$ alkoxy, $C_1$–$C_4$ alkoxy($C_1$–$C_4$)alkyl, mono($C_1$–$C_4$) alkylamino($C_1$–$C_4$)alkyl, di($C_1$–$C_4$)alkylamino ($C_1$–$C_4$)alkyl, $C_1$–$C_4$ perfluoroalkyl, cyano($C_1$–$C_4$) alkyl and carboxy($C_1$–$C_4$)alkyl radicals or an amino group.

15. A method according to claim 14, wherein said keratinous fiber is human keratinous fiber.

16. A method according to claim 15, wherein said human keratinous fiber is hair.

17. A process for oxidation dyeing of keratinous fiber comprising the steps of:

applying to keratinous fiber at least one dyeing composition composition according to claim 1; and thereafter developing colour at acidic, neutral or alkaline pH with at least one oxidizing agent, wherein said at least one oxidizing agent is added at the time of use to said dyeing composition or said at least one oxidizing agent is present in a separate oxidizing composition applied simultaneously with or sequentially to said dyeing composition.

18. A process according to claim 17, wherein said keratinous fiber is human keratinous fiber.

19. A process according to claim 18, wherein said human keratinous fiber is hair.

20. A process according to claim 17, wherein said at least one oxidizing agent is selected from hydrogen peroxide, urea hydrogen peroxide, alkali metal bromates, persalts, peracids and enzymes.

21. A process according to claim 20, wherein said persalts are selected from perborates and persulphates.

22. A multi-compartment device or multi-compartment dyeing kit comprising a first compartment containing at least one dyeing composition according to claim 1 and a second compartment containing at least one oxidizing composition.

23. A composition for dyeing keratinous fiber comprising, in a medium appropriate for dyeing:

at least one coupler selected from indazoleamine derivatives of formula (I) and acid addition salts thereof:

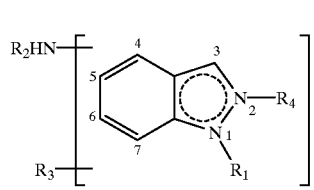

(I)

in which:

$R_1$ denotes a radical selected from $C_1$–$C_4$ alkyl, $C_1$–$C_4$ hydroxyalkyl, $C_1$–$C_4$ aminoalkyl, mono($C_1$–$C_4$) alkylamino($C_1$–$C_4$)alkyl, di($C_1$–$C_4$)alkylamino ($C_1$–$C_4$)alkyl, ($C_1$–$C_4$)alkoxycarbonyl, ($C_1$–$C_4$) alkoxycarbonyl($C_1$–$C_4$)alkyl, $C_1$–$C_4$ acyl, ($C_1$–$C_4$) alkoxy($C_1$–$C_4$)alkyl, cyano($C_1$–$C_4$)alkyl, allyl and ($C_1$–$C_4$)alkylthiocarbonyl($C_1$–$C_4$)alkyl radicals and then $R_4$ forms a double bond with the carbon in the 3 position;

$R_2$ denotes a hydrogen atom or a radical selected from $C_1$–$C_4$ alkyl, $C_1$–$C_4$ hydroxyalkyl, $C_1$–$C_4$ aminoalkyl, mono($C_1$–$C_4$)alkylamino($C_1$–$C_4$)alkyl, di($C_1$–$C_4$) alkylamino($C_1$–$C_4$)alkyl, carboxy($C_1$–$C_4$)alkyl, ($C_1$–$C_4$)alkoxyl($C_1$–$C_4$)alkyl and ω-hydroxy($C_1$–$C_4$) alkoxy($C_1$–$C_4$)alkyl radicals; and $R_3$ denotes a hydrogen atom, a bromine, chlorine or fluorine atom, or a radical selected from $C_1$–$C_4$ alkyl, $C_1$–$C_4$ hydroxyalkyl, $C_1$–$C_4$ aminoalkyl, $C_1$–$C_4$ alkoxy, $C_1$–$C_4$ alkoxy ($C_1$–$C_4$)alkyl, mono($C_1$–$C_4$) alkylamino($C_1$–$C_4$)alkyl, di($C_1$–$C_4$)alkylamino ($C_1$–$C_1$–$C_4$)alkyl, $C_1$–$C_4$ perfluoroalkyl, cyano($C_1$–$C_4$) alkyl and carboxy($C_1$–$C_4$)alkyl radicals; or $R_4$ denotes a radical selected from $C_1$–$C_4$ alkyl, $C_1$–$C_4$ hydroxyalkyl, $C_1$–$C_4$ aminoalkyl, mono($C_1$–$C_4$)alkylamino($C_1$–$C_4$)alkyl, di($C_1$–$C_4$)alkylamino($C_1$–$C_4$)alkyl, ($C_1$–$C_4$)alkoxycarbonyl, $C_1$–$C_4$ acyl and $C_7$–$C_9$ alkylaryl radicals and an amidino radical (—C(NH$_2$)=NH) and then $R_1$ forms a double bond with the carbon adjacent to the nitrogen atom bonded to $R_1$;

$R_2$ denotes a hydrogen atom or a radical selected from $C_1$–$C_4$ alkyl, $C_1$–$C_4$ hydroxyalkyl, $C_1$–$C_4$ aminoalkyl, mono($C_1$–$C_4$)alkylamino($C_1$–$C_4$)alkyl, di($C_1$–$C_4$)alkylamino($C_1$–$C_4$)alkyl, carboxy($C_1$–$C_4$)alkyl, ($C_1$–$C_4$)alkoxy($C_1$–$C_4$)alkyl and ω-hydroxy($C_1$–$C_4$)alkoxy($C_1$–$C_4$)alkyl radicals; and $R_3$ denotes a hydrogen atom, a bromine, chlorine or fluorine atom, or a radical selected from $C_1$–$C_4$ alkyl, $C_1$–$C_4$ hydroxyalkyl, $C_1$–$C_4$ aminoalkyl, $C_1$–$C_4$ alkoxy, $C_1$–$C_4$ alkoxy ($C_1$–$C_4$)alkyl, mono($C_1$–$C_4$)alkylamino($C_1$–$C_4$)alkyl, di($C_1$–$C_4$)alkylamino($C_1$–$C_4$)alkyl, $C_1$–$C_4$ perfluoroalkyl, cyano($C_1$–$C_4$)alkyl and carboxy($C_1$–$C_4$)alkyl radicals or an amino group;

and at least one heterocyclic oxidation base.

24. A composition according to claim 23 wherein said at least one heterocylic oxidation base is selected from pyrazolopyrimidine compounds and pyrazole compounds.

25. A composition for dyeing keratinous fiber comprising, in a medium appropriate for dyeing:

at least one coupler selected from indazoleamine derivatives of formula (I) and acid addition salts thereof:

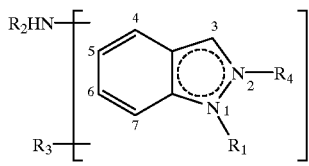

(I)

in which:

either $R_1$ denotes a hydrogen atom or a radical selected from $C_1$–$C_4$ alkyl, $C_1$–$C_4$ hydroxyalkyl, $C_1$–$C_4$ aminoalkyl, mono($C_1$–$C_4$)alkylamino($C_1$–$C_4$)alkyl, di($C_1$–$C_4$)alkylamino($C_1$–$C_4$)alkyl, ($C_1$–$C_4$)alkoxycarbonyl, ($C_1$–$C_4$)alkoxycarbonyl($C_1$–$C_4$)alkyl, $C_1$–$C_4$ acyl, ($C_1$–$C_4$)alkoxy($C_1$–$C_4$)alkyl, cyano($C_1$–$C_4$)alkyl, allyl and ($C_1$–$C_4$)alkylthiocarbonyl ($C_1$–$C_4$)alkyl radicals and then $R_4$ forms a double bond with the carbon in the 3 position; or $R_4$ denotes a radical selected from $C_1$–$C_4$ alkyl, $C_1$–$C_4$ hydroxyalkyl, $C_1$–$C_4$ aminoalkyl, mono($C_1$–$C_4$)alkylamino($C_1$–$C_4$)alkyl, di($C_1$–$C_4$)alkylamino ($C_1$–$C_4$)alkyl, ($C_1$–$C_4$)alkoxycarbonyl, $C_1$–$C_4$ acyl and $C_7$–$C_9$ alkylaryl radicals and an amidino radical (—C(NH$_2$)=NH) and then $R_1$ forms a double bond with the carbon adjacent to the nitrogen atom bonded to $R_1$;

$R_2$ denotes a hydrogen atom or a radical selected from $C_1$–$C_4$ alkyl, $C_1$–$C_4$ hydroxyalkyl, $C_1$–$C_4$ aminoalkyl, mono($C_1$–$C_4$)alkylamino($C_1$–$C_4$)alkyl, di($C_1$–$C_4$)alkylamino($C_1$–$C_4$)alkyl, carboxy($C_1$–$C_4$)alkyl, ($C_1$–$C_4$)alkoxy($C_1$–$C_4$)alkyl and ω-hydroxy($C_1$–$C_4$)alkoxy($C_1$–$C_4$)alkyl radicals;

$R_3$ denotes a hydrogen atom, a bromine, chlorine or fluorine atom, or a radical selected from $C_1$–$C_4$ alkyl, $C_1$–$C_4$ hydroxyalkyl, $C_1$–$C_4$ aminoalkyl, $C_1$–$C_4$ alkoxy, $C_1$–$C_4$ alkoxy ($C_1$–$C_4$)alkyl, mono($C_1$–$C_4$)alkylamino($C_1$–$C_4$)alkyl, di($C_1$–$C_4$)alkylamino ($C_1$–$C_4$)alkyl, $C_1$–$C_4$perfluoroalkyl, cyano($C_1$–$C_4$)alkyl and carboxy($C_1$–$C_4$)alkyl radicals or an amino group;

wherein:

when $R_1$ represents a hydrogen atom and when $R_4$ forms a double bond with the carbon in the 3 position and when $R_2$ represents a hydrogen atom or a $C_1$–$C_4$ alkyl radical, then $R_3$ cannot represent an amino group in the meta position with respect to the —NHR$_2$ group;

when $R_1$ and $R_2$ simultaneously represent a hydrogen atom and when $R_4$ forms a double bond with the carbon in the 3 position, then $R_3$ is other than a $C_1$ alkoxy radical;

and at least one heterocyclic oxidation base selected from pyrazolopyrimidine compounds and pyrazole compounds.

* * * * *

UNITED STATES PATENT AND TRADEMARK OFFICE
CERTIFICATE OF CORRECTION

PATENT NO. : 6,027,538
DATED : February 22, 2000
INVENTOR(S) : Jean Jacques VANDENBOSSCHE et al.

It is certified that error appears in the above-indentified patent and that said Letters Patent is hereby corrected as shown below:

TITLE:

Front page, item [73], change "Assignee: L'Oreal S.A." to --Assignee: L'Oreal, S.A.--

IN THE CLAIMS:

Claim 1, col. 12, line 36, after "alkylamino($C_1$-$C_4$)alkyl", insert --,--
Claim 23, col. 16, line 66, "($C_1$-$C_1$-$C_4$)alkyl" should read --($C_1$-$C_4$)alkyl--.

Signed and Sealed this

Third Day of April, 2001

Attest:

NICHOLAS P. GODICI

Attesting Officer     Acting Director of the United States Patent and Trademark Office